United States Patent [19]

Lombardi

[11] Patent Number: 4,722,343
[45] Date of Patent: Feb. 2, 1988

[54] METHOD AND APPARATUS FOR APPLYING ELECTRICAL STIMULUS PULSES TO A SUBJECT

[75] Inventor: Daniel J. Lombardi, Verona, Wis.

[73] Assignee: Nicolet Instrument Corporation, Madison, Wis.

[21] Appl. No.: 809,496

[22] Filed: Dec. 16, 1985

[51] Int. Cl.[4] ............................................. A61N 1/36
[52] U.S. Cl. ..................................... 128/421; 128/741
[58] Field of Search ..................... 128/741, 419 R, 421

[56] References Cited

U.S. PATENT DOCUMENTS

| | | | |
|---|---|---|---|
| 3,320,947 | 5/1967 | Knoll | 128/741 |
| 4,185,640 | 1/1980 | Kastrubin et al. | 128/421 |
| 4,354,498 | 10/1982 | Welgert et al. | 128/419 R |
| 4,363,324 | 12/1982 | Kusserow | 128/419 R |
| 4,510,936 | 4/1985 | Fourcin et al. | 128/419 R |
| 4,600,010 | 7/1986 | Dugot | 128/421 |

OTHER PUBLICATIONS

Kevin C. McGill et al., "On the Nature and Elimination of Stimulus Artifact in Nerve Signals Evoked and Recorded Using Surface Electrodes," IEEE Trans. on Biomedical Engineering, vol. BME-29, No. 2, Feb., 1982, pp. 129–136.

*Primary Examiner*—William G. Kamm
*Attorney, Agent, or Firm*—Isaksen, Lathrop, Esch, Hart & Clark

[57] ABSTRACT

A method and apparatus for stimulating evoked potentials in a human subject maintains the common mode voltage at the stimulation electrodes substantially constant both before and during application of a stimulus pulse of constant current. A pair of resistors are connected between the stimulation electrodes and are joined at a reference node. One stimulation electrode (e.g., the anode) is connected through a field effect transistor to the power supply voltage and the other electrode (e.g., the cathode) is connected to the supply common return through a transistor which, when turned on, is controlled to conduct a constant current. The voltage at the reference node is supplied to the gate of a second field effect transistor which has its source clamped to a reference voltage. The voltage at the drain of the second field effect transistor is supplied back to the gate of the first field effect transistor. The two field effect transistors cooperate to supply a voltage to the anode electrode which is controlled such that the voltage at the reference node remains substantially constant before, during and after the switching transistor switches to provide a stimulation pulse. The common mode voltage at the anode and cathode is thus maintained substantially constant during stimulation pulses to minimize stimulus artifacts at the sensing electrodes.

29 Claims, 2 Drawing Figures

METHOD AND APPARATUS FOR APPLYING ELECTRICAL STIMULUS PULSES TO A SUBJECT

FIELD OF THE INVENTION

This invention pertains generally to the field of evoked potential testing and particularly to instruments which apply electrical pulses to an individual to stimulate evoked potentials.

BACKGROUND ART

Evoked potential measurements are now commonly made in clinical practice and in research to evaluate nervous system functions. To measure the evoked potentials stimulated by electrical pulses, surface measurement electrodes are customarily positioned on the scalp or skin over peripheral nerves. The electrical potentials received by these electrodes are detected and analyzed by sensitive recording equipment. To stimulate a response in the nervous system, stimulation electrodes are applied to the skin of the subject at a position remote from the measurement electrodes, typically on an arm or leg, and a pulse of either constant voltage or constant current magnitude is then applied to the individual between the two stimulation electrodes.

A ground strap or electrode is conventionally placed on the individual being tested at a position between the stimulation electrodes and the measurement electrodes. The grounded electrode maintains the mean voltage of the limb to which it is mounted near ground and prevents current passing through vital organs if the stimulation equipment should short circuit. The electrical circuit which delivers the stimulation pulse is electrically isolated from ground so that no net current should pass through the individual to ground from the stimulating electrodes. However, it is observed with conventional stimulation instruments that the large common mode transient voltage appearing at the electrodes at the time of a pulse causes displacement current to flow through the inherent parasitic capacitance of the patient to the patient referenced ground or common. This "escape" displacement current creates a voltage transient at the measurement electrodes that can saturate the physiological amplifiers for several milliseconds following the stimulus pulse, thereby obscuring or interfering with the recording of pertinent evoked potential data. See K. C. McGill, et al., "On the nature and elimination of stimulus artifact in nerve signals evoked and recorded using surface electrodes," IEEE Trans. Biomed. Engr., Vol. BME-29, No. 2, pp. 129-137, February 1982.

As explained in the foregoing article, the common mode voltage at the recording site is the sum of (1) the voltage dropped between the grounding and recording sites by the stimulus current, and (2) the voltage dropped across the ground electrode by the escape current. At the rising and falling edges of the stimulus pulse, the stray stimulator capacitances must be charged and discharged. Unless the capacitances and the stimulating electrode impedances are perfectly balanced, this results in escape current flow through the ground electrode.

SUMMARY OF THE INVENTION

In accordance with the present invention, the common mode voltage at the stimulation electrodes with respect to the stimulation circuit common is maintained substantially constant both before and during application of a stimulus pulse between the electrodes. Consequently, substantially no escape displacement current flows through the parasitic capacitance to the patient ground as a result of common mode transient voltage, thereby minimizing stimulus artifacts in the measured potential which otherwise could interfere with signal analysis and possibly saturate the physiological amplifier.

The apparatus for applying the stimulus pulse includes a pair of resistors, preferably equal in resistance, connected between the anode and cathode electrodes and electrically connected together at a reference node. A switchable circuit element is connected between one of the electrodes and the common return for the stimulator power source—which is electrically isolated from the subject—and can switch between a non-conducting state and a conducting state. A controllable conduction element is connected between the power source and the other electrode. A control circuit is connected to the reference node and to the controllable conduction element to provide a control signal to it. The control circuit and controllable conduction element cooperate to control the voltage from the power source applied across the stimulation electrodes to maintain the voltage at the reference node substantially constant.

Initially, when the switchable element is in a non-conducting or open state, the control circuit provides a control signal to the controllable conduction element to maintain the voltage at the reference node at a selected value. The effective resistance of the controllable conduction element is adjusted such that the voltage from the power source dropped across the controllable element is essentially equal to the voltage dropped between the second electrode and the power source common. The switchable element is selectively switchable, as in response to a signal from the operator, to switch to a conductive state. When this happens, a circuit is completed between the stimulation electrodes through the subject and also, in parallel therewith, through the pair of resistors, to the switchable element and back to the power source common. The control circuit continues to monitor the voltage at the reference node and provides appropriate control signals, in closed loop feedback fashion, to the controllable conduction element to maintain the voltage at the reference node substantially constant.

In a preferred embodiment, the controllable conduction element comprises a first field effect transistor with its source and drain connected between the power source and one of the electrodes. The control circuit includes another field effect transistor (FET) having its gate connected to the reference node and its source clamped to a reference voltage, and configured to supply an output voltage to the gate of the first field effect transistor. The output voltage of the second FET controls the gate to source voltage of the first FET such that the drain to source voltage thereof is appropriate to maintain the reference node voltage substantially constant. The switchable element preferably includes a transistor configured to maintain a constant current stimulation pulse when in its conducting state.

Further objects, features, and advantages of the invention will be apparent from the following detailed description when taken in conjunction with the accompanying drawings.

DESCRIPTION OF THE PREFERRED EMBODIMENT

Figure 1:
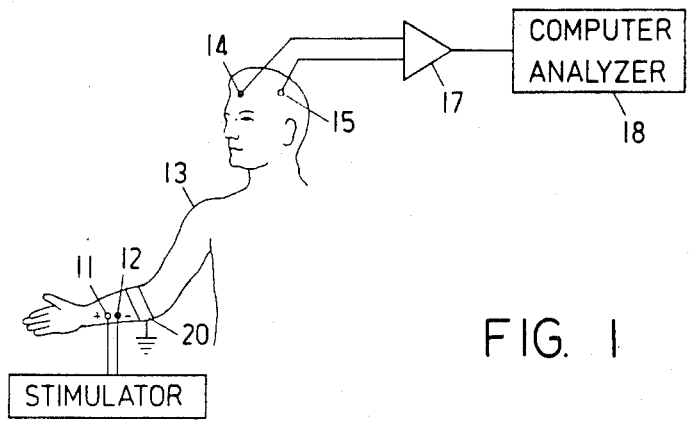
FIG. 1 is a pictorial view illustrating the application of the stimulator apparatus to an individual for evoked potential testing.

With reference to the drawings, a pictorial view illustrating a typical application of the stimulation apparatus of the invention is shown generally at 10 in FIG. 1 in position to apply a stimulation pulse between an anode electrode 11 and cathode electrode 12, each of which is mounted to a human subject 13. The anode and cathode electrodes 11 and 12 may be of any of the various common electrodes utilized for evoked potential stimulation. Sensing electrodes 14 and 15 are attached to the subject at locations determined in accordance with standard clinical practice for measuring selected evoked potentials. The sensing electrodes 14 and 15 are connected to a physiological amplifier, shown for illustration at 17 in FIG. 1, the output of which may be provided to a recorder or to a computer analyzer 18 for appropriate analysis. For example, the computer analyzer may perform "averaging" on the waveforms received from multiple stimulations to extract the evoked potentials from random background signals.

It is conventional practice to attach a grounding strap or electrode 20 to the subject at a location between the stimulation electrodes 11 and 12 and the sensing electrodes 14 and 15. Despite use of such a grounding electrode, it has been found that a large common mode transient voltage at the stimulator electrodes 11 and 12 causes displacement current to flow through parasitic capacitance to the patient common, resulting in artifact voltage transients at the sensing electrodes 14 and 15 which may be sufficient to saturate the physiological amplifier for several milliseconds following initiation of a stimulation pulse.

Figure 2:
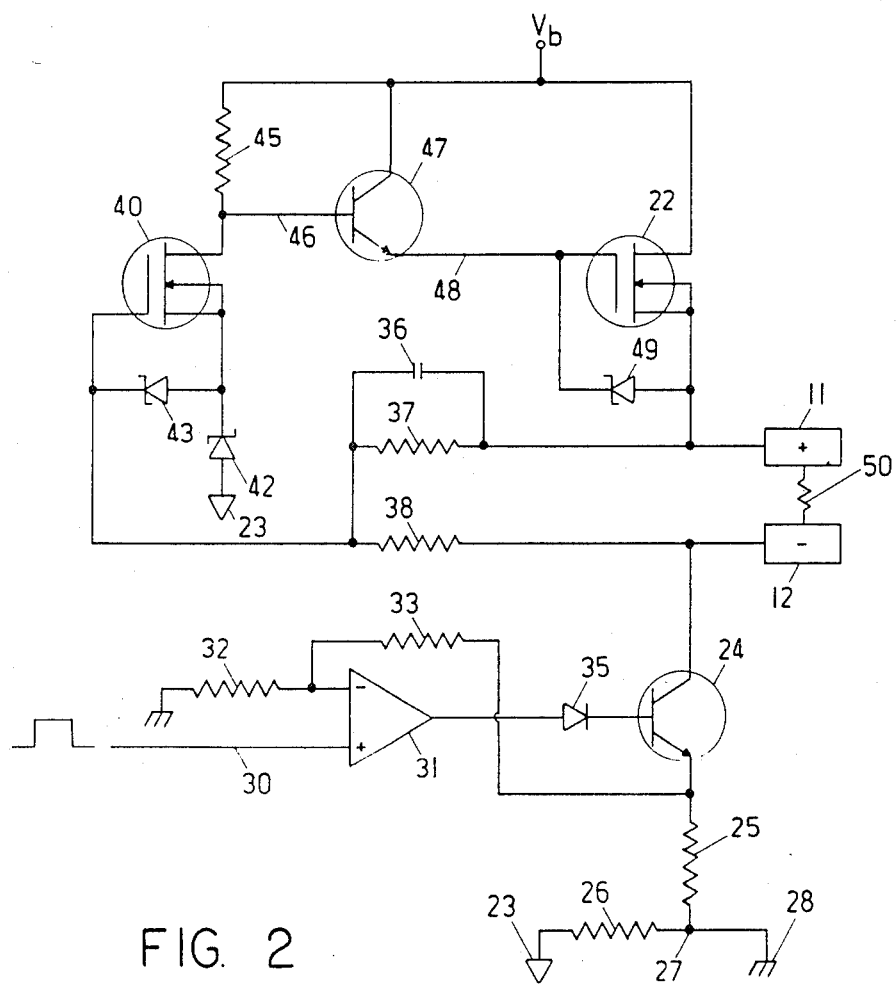
FIG. 2 is a schematic circuit diagram of a stimulator apparatus in accordance with the invention.

A preferred embodiment of a stimulator apparatus circuit 10 for providing constant current stimulation pulses to the electrodes 11 and 12 while maintaining a substantially constant common mode voltage is shown in FIG. 2. A power source (not shown in FIG. 2) which provides a DC supply voltage $V_b$ is connected to the anode electrode 11 through a first field effect transistor 22, which provides controllable conduction therethrough, and the cathode electrode 12 is connected to the common return 23 of the power source through an NPN bipolar transistor 24, a first load resistor 25, and a second load resistor 26. The junction 27 between the resistors 25 and 26 is connected to the return 28 for the stimulator. In accordance with conventional practice, the power supply common return 23 and the stimulator return 28 are isolated from the ground or common for the subject 20. The transistor 24 can be selectively switched from a non-conducting state in which the current is conducted between the anodes 11 and 12 to a conducting state in which a selected current is passed between the electrodes 11 and 12.

The conduction through the transistor 24 is controlled by a signal on an input line 30 received at the positive or non-inverting input of an operational amplifier 31. The input signal on the line 30 will be a drive pulse of variable voltage magnitude, with the magnitude of the pulse height being proportional to the desired magnitude of the current pulse between the electrodes 11 and 12. For example, the signal on the line 30 may be provided in a known fashion from the computer analyzer 18 which controls the magnitude, frequency and duration of stimulus pulses. A resistor 32 is connected between the stimulator return and the negative or inverting input of the amplifier 31 and a feedback resistor 33 is connected between the emitter of the transistor 24 and the inverting input of the amplifier 31, thus forming a voltage divider which applies a selected fraction of the emitter voltage to the inverting input of the amplifier 31. The output of the amplifier 31 on a line 34 is passed through a diode 35 to the base of the transistor 24. Thus, when the line 30 is initially at a low or zero volt condition (with respect to stimulator common), the output of the amplifier 31 will be low and the transistor 24 will be cut off. When a positive voltage pulse is received on the line 30, the output of the amplifier 31 will go high and it will be passed through the diode 35 to the base of the transistor 24, turning it on. As current flows through the transistor 24 into the resistor 25, the increasing voltage at the emitter of the transistor 24 is fed back through the resistor 33 to the inverting input of the amplifier 31, stabilizing the voltage across the emitter resistor 25, and thus the current passed by the transistor 24, at a level proportional to the magnitude of the voltage of the input pulse on the line 30.

A pair of resistors 37 and 38, preferably of equal resistance, are connected in series between the anode electode 11 and cathode electrode 12. A capacitor 36 of relatively small capacity is connected across the resistor 37 to enhance the response time of the circuit. The resistors 37 and 38 are electrically joined at a reference node 39. Th resistance of each of the resistors 37 and 38 is substantially greater than the resistance of the subject to current flowing between the anode and cathode. Thus, when the transistor 24 is switched on, most of the current flowing through it will flow through the subject rather than through the resistors 37 and 38. In conventional stimulation apparatus, when a current pulse is applied to the subject the transient common mode voltage of the anode and cathode may shift substantially with respect to the stimulation power supply common or to reference voltages in other parts of the physiological amplifier 17 or computer analyzer 18 and related apparatus. Substantial transient voltage artifacts may appear at the sensing electrodes as a result of the rapid shift in the common mode voltage at the anode and cathode. In the present invention, the common mode voltage at the anode 11 and cathode 12 is stabilized by controlling the voltage at the reference node 39 to be substantially constant before, during and after application of a stimulation current pulse.

In the preferred embodiment circuit of FIG. 2, the voltage at the node 39 is provided to the gate of a second field effect transistor (FET) 40. A zener diode 42, preferably having a nominal zener breakover voltage approximately equal to one-half of $V_b$, is connected between the source of the transistor 40 and the power supply common return 23. The zener diode 42 thus serves to clamp the source terminal of the FET 40 at the zener breakover voltage. Another zener diode 43 is connected between the gate and source of the transistor 40 to normally isolate the source and gate but conduct under overload conditions, while the drain terminal of the transistor is connected to the supply voltage $V_b$ through a resistor 45. The transistor 40 is thus configured as a common source amplifier. The voltage at the drain of the transistor 40 is provided on a line 46 to the base of an NPN bipolar transistor 47 having its collector directly connected to the supply voltage $V_b$ and its emitter connected by a line 48 to the gate of the transistor 22. A zener diode 49 is connected between the gate and the source of the transistor 22 to normally isolate the two terminals but conduct under overload conditions.

The stabilization of the voltage at the reference node 39 occurs in the following manner. The steady state voltage at the reference node 39 will be established at a level equal to the nominal zener breakover voltage of the zener diode 42 (preferably about one-half $V_b$) plus the gate threshold voltage of the FET 40 (e.g., typically 2 to 4 volts). Because the transistor 22 is configured as a source follower, the foregoing voltage at the node 39 is the only voltage that allows each of the transistors 40 and 22 to satisfy their gate to source voltage requirements as a consequence of the negative feedback from the common source amplifier 40, fed to the gate of the transistor 22 through the transistor 47. When a current drive pulse occurs on the line 30, the transistor 24 is turned on and, as current begins to pass between the anode and cathode electrodes, the voltage level at the cathode 12 begins to pull below its steady state value (equal to the voltage level at the node 39). The amount of current passing through the subject between the anode and cathode electrodes will be proportional to the amplitude of the drive pulse on the line 30 and the voltage gain of the amplifier 31. However, when the cathode 12 begins to go low, the circuit will become unbalanced since current will tend to be drawn through the resistor 38, drawing the voltage at the node 39 low also. The decrease in the gate to source voltage on the transistor 40 causes it to restrict the current passing between the drain and source thereof, driving the line 46 and thence the line 48 high, and increasing the gate to source voltage on the transistor 22. This results in a decrease in the effective resistance of the transistor 22 and a drop in the voltage across it, thereby tending to push the voltage at the anode 11 high at the same time that the voltage at the cathode 12 is pulled low, such that the changes in voltages at the anode and cathode complement one another. As a consequence, the common mode voltage at the reference node 39 remains constant both before, during and after the stimulation pulse.

The FET transistor 22 thus functions as a controllable conduction means for controlling the voltage dropped between its source and drain in response to a control signal provided to its gate on the line 48. The transistors 40 and 47, with their associated biasing circuits, are configured to receive the voltage level at the reference node 39 and provide a means for controlling the conduction of the transistor 22 by providing an appropriate control voltage on the line 48 to the gate of the transistor 22. The transistor 24 and the drive circuitry composed of the amplifier 31 and the associated resistors 25, 26, 32 and 33 provide a switchable circuit means for responding to a selected input signal on the line 30 to switch the transistor 24 from a non-conducting state to a conducting state in which the current passed by the transistor 24 is controlled to be proportional to the magnitude of the voltage level of the pulse input signal on the line 30.

Prior to and between stimulation pulses, the transistor 24 is at (or near) cut-off. Any current flowing through the transistor 22 at this time divides between the resistor 37 and the subject impedance 50. The cut-off transistor 24 (and, to some extent, the back biased zener diode 43) allows a slight current flow from the cathode electrode connection at a high but finite effective resistance. Thus, at the initial operating condition, the gate to source voltage across the transistor 40 controls the voltage level at the drain of the transistor 40, and thus the output voltage from the transistor 47 on the line 48, so that the gate to source voltage on the transistor 22 is just sufficient to provide a very high drain to source resistance for the transistor 22, which may effectively match the magnitude of the resistance through the transistor 24 or other circuit components back to the supply common 23. If the resistors 37 and 38 are of equal resistance, and if the voltage at which the source of the transistor 40 is clamped is about $\frac{1}{2} V_b$, then the voltage at the reference node 39 will be $\frac{1}{2} V_b$ plus the gate to source voltage of transistor 40 (e.g., 2 to 4 volts).

When a current stimulation control pulse is received on the line 30, the transistor 24 is turned on, which drops the voltage at the cathode 12—relative to supply common—, and consequently also drops the voltage at the node 39. Since the voltage at the source of the transistor 40 is fixed by the zener diode 42, the gate to source voltage decreases, resulting in an increase in the drain to source voltage at the line 46. This voltage is supplied through the transistor 47 on the line 48 to the gate of the transistor 22, resulting in a decrease in the voltage across the transistor and an increase in the current through the transistor. As described above, the transistor 24 is controlled to supply a fixed maximum current for a particular voltage magnitude of the input pulse on the line 30, and the same current is passed through the transistor 22. The supply voltage $V_b$ is thus dropped in turn across the transistor 22, the parallel combination of the series resistors 37 and 38 with the subject impedance 50, the transistor 24, and the series resistors 25 and 26. The voltage applied between the anode 11 and cathode 12 to the subject is divided across the resistors 37 and 38. If the resistors are of equal resistance, the voltage at the node 39 will be at one-half of the difference between the voltages at the anode and cathode. The voltage at the node 39 clearly cannot drop below the breakover voltage of the zener diode 42 (e.g., about one-half $V_b$). The drain to source voltage of the transistor 22 thus decreases an amount sufficient so that the voltage applied between the anode and cathode dividing across the resistors 37 and 38 at the node 39 remains substantially at one-half $V_b$; i.e., the voltage dropped across the transistor 22 is substantially equal to the voltage dropped across the transistor 24 and the resistors 25 and 26. In this manner, the voltages at the anode electrode 11 and cathode electrode 12 will increase and decrease, respectively, an equal amount during a current pulse from the steady state voltage at these electrodes such that there is substantially no change in the common mode voltage suppled to the subject.

A specific example of a circuit for implementing the apparatus in accordance with the invention includes the following part number and component values:

Transistors 22 and 40: MOSFET VN0540
Transistor 47: 2N6512
Transistor 24: 2N3439
Amplifier 31: LM356
Zener Diodes 43 and 49: IN5245
Zener Diode 42: IN5276B
Diode 35: IN4006

Capacitor 36: 33 pf
Resistor 25: 125 ohms
Resistor 26: 50 ohms
Resistor 32: 10K ohms
Resistor 33: 2.49K ohms
Resistor 37: 100K ohms
Resistor 38: 100K ohms
Resistor 45: 1M ohms The power supply unit providing the voltage $V_b$ should be isolated from the subject ground and frame common, and may constitute, for example, a regulated DC power supply receiving line power through an isolation transformer or a battery. A suitable supply voltage for the component values listed above is 300 volts, providing a substantially constant voltage at the reference node 39 slightly greater than 150 volts.

It is understood that the invention is not confined to the particular embodiment illustrated and described herein, but embraces such modified forms thereof as come within the scope of the following claims.

What is claimed is:

1. An apparatus for receiving voltage from a source of electrical power having a common return and applying an electrical stimulation pulse to a subject through anode and cathode stimulation electrodes, comprising:
   (a) a pair of resistors electrically connected between the anode and cathode electrodes and electrically joined to define a reference node;
   (b) controllable conduction means, electrically connected to one of the electrodes and including means for connecting to the source of electrical power, for responding to a control signal to control selectively the current passed therethrough and the voltage thereacross;
   (c) switchable means, electrically connected to the other of the stimulation electrodes and including means for connecting to the source of electrical power to return current to the souce of electrical power, for selectively switching between a non-conducting state and a conducting state;
   (d) control means, connected to the reference node and to the controllable conduction means, for responding to the voltage of the reference node to provide a control signal to the controllable conduction means so as to maintain the voltage at the reference node substantially constant as the switchable means is switched from the non-conducting state to the conducting state.

2. The apparatus of claim 1 wherein the two resistors in the pair are of equal resistance.

3. The apparatus of claim 1 wherein the controllable conducting means comprises a field effect transistor havings its drain and source connected between the power source and the one electrode, and receiving the control signal at its gate.

4. The apparatus of claim 1 wherein the switchable means includes means for controlling the current passed therethrough to a selected level when in its conducting state.

5. The apparatus of claim 4 wherein the switchable means is responsive to an input voltage pulse to switch from the non-conducting to the conducting state and wherein the level of the current passed therethrough in the conducting state is controlled to be directly proportional to the magnitude of the voltage of the input pulse.

6. The apparatus of claim 1 wherein the control means includes a field effect transistor connected in a common source configuration with its drain connected through a resistor to receive voltage from the power source and its source connected through a zener diode to return current to the power source, the zener diode having a selected breakover voltage, and wherein the gate of the field effect transistor is connected to the reference node and the voltage at the drain is operably connected to the controllable conduction means to provide a voltage control signal.

7. The apparatus of claim 6 including a bipolar transistor having its collector available to be connected to the source of electrical power, its gate connected to the drain of the field effect transistor and its emitter connected to provide the control signal to the controllable conduction means.

8. The apparatus of claim 1 wherein the switchable means includes a bipolar transistor having its collector connected to one of the electrodes and its emitter connected to a load resistor which is available to be connected to the power source common return and including means responsive to a voltage input pulse signal which may be supplied thereto and to the voltage at the emitter to provide input current to the base of the transistor to control the current passing between the collector and emitter at a selected current level proportional to the voltage of the input pulse.

9. The apparatus of claim 8 wherein the means responsive to provide input current to the bipolar transistor includes an operational amplifier having its output connected to the base of the transistor and receiving the input pulse signal at a first non-inverting input terminal and further connected to the emitter of the transistor through a voltage divider to provide a feedback voltage signal to a second inverting input of the operational amplifier.

10. A stimulator apparatus receiving voltage from a voltage source having a common return and applying an electrical stimulation pulse to a subject through anode and cathode electrodes, comprising:
   (a) a pair of resistors electrically connected between the anode and cathode electrodes and electrically joined to define a reference node;
   (b) a first field effect transistor having gate, drain and source terminals, one of the drain or source terminals connected to one of the electrodes, and the other of the source or drain terminals connected to the voltage source;
   (c) switchable means, electrically connected to the other of the electrodes and connected to return current to the voltage source, for selectively switching between a non-conducting state and a conducting state;
   (d) a second field effect transistor having gate, source and drain terminals, the gate terminal connected to the reference node to receive the voltage at the node, means for clamping the voltage of the source terminal at a selected voltage level, and resistance means connected to the drain and connected to the voltage source for biasing the second field effect transistor at a selected level, and circuit means for transmitting the voltage level at the drain of the second field effect transistor to the gate of the first field effect transistor, whereby the voltage dropped across the first transistor will be controlled such that the voltage at the reference node with respect to the common return of the voltage source will be maintained substantially constant at a level near the voltage at which the source of the second transistor is clamped as the switchable means switches between its non-conducting state and its conducting state.

11. The apparatus of claim 10 wherein the means for clamping the source of the second field effect transistor at a selected voltage level comprises a zener diode connected between the source of the second transistor and the common return to the voltage source.

12. The apparatus of claim 10 wherein the two resistors in the pair are of equal resistance.

13. The apparatus of claim 10 wherein the means for transmitting voltage from the drain of the second transistor to the gate of the first transistor includes a bi-polar transistor having its base connected to the source of the second transistor, its emitter connected to the gate of the first transistor, and its collector connected to the voltage source.

14. The apparatus of claim 10 wherein the switchable means includes means for controlling the current passed therethrough to a selected level when in its conducting state.

15. The apparatus of claim 14 wherein the switchable means further comprises means responsive to a voltage pulse for switching from the non-conducting to the conducting state and means for controlling the level of the current passed therethrough in the conducting state to be directly proportional to the magnitude of the voltage of the input pulse signal.

16. The apparatus of claim 10 wherein the switchable means includes: a bipolar transistor having its collector connected to one of the electrodes and its emitter connected to a load resistor which is connected to the voltage source common return and including means responsive to a voltage input pulse signal which may be provided thereto and to the voltage at the emitter for providing input current to the base of the transistor to control the current passing between the collector and emitter at a selected current level proportional to the voltage of the pulse input signal.

17. The apparatus of claim 16 wherein the means responsive for providing current to the base of the bipolar transistor includes an operational amplifier having its output connected to the base of the transistor and receiving the input pulse signal at a first non-inverting input terminal and further connected to the emitter of the transistor through a voltage divider to provide a feedback voltage signal to a second inverting input of the operational amplifier.

18. A method of applying electrical stimulation to a subject through anode and cathode stimulation electrodes which are applied to the subject, comprising the steps of:
 (a) electrically connecting a pair of resistors, which are joined together at a reference node, between the anode and cathode electrodes;
 (b) providing a voltage source and a voltage common return line isolated from the patient;
 (c) selectively connecting a first of the anode and cathode electrodes by a conducting path to the common return line when a stimulation pulse is to be provided between the electrodes and providing no conducting path to the common return line from the first electrode when no stimulation pulse is to be provided; and
 (d) supplying a voltage to the second of the anode and cathode electrodes at a level controlled such that the voltage at the reference node with respect to the common return remains substantially constant both when there is and is not a conducting path between the first electrode and the common return.

19. The method of claim 18 wherein the step of selectively providing a conducting path between the first electrodes and the common return includes the step of maintaining the current flowing from the first electrode to the common return at a substantially constant level as long as the conducting path is maintained.

20. An apparatus receiving voltage from a source of electrical power having a common return and for applying an electrical stimulation pulse to a subject through anode and cathode stimulation electrodes, comprising:
 (a) resistance means electrically connected between the anode and cathode electrodes for providing a resistive voltage drop therebetween and having a reference node;
 (b) switchable means, electrically connected to one of the anode and cathode electrodes and connected to the common return, for selectively switching between a non-conducting state and a conducting state;
 (c) means, connected to the reference node, the power source, and to the other of the anode and cathode electrodes, for supplying a voltage level to that electrode at a level controlled such that the voltage at the reference node with respect to the common return will be substantially constant when the switchable means is in the non-conducting state and in the conducting state.

21. The apparatus of claim 20 wherein the means for supplying a voltage level includes:
 (1) controllable conduction means, electrically connected to one of the electrodes and to the source of electrical power, for responding to a control signal which may be provided thereto to selectively control the current passed therethrough and the voltage theracross;
 (2) control means, connected to the reference node and to the controllable conduction means, for responding to the voltage of the reference node to provide a control signal to the controllable conduction means so as to maintain the voltage at the reference node substantially constant as the switchable means is switched from the non-conducting state to the conducting state.

22. The apparatus of claim 21 wherein the controllable conduction means comprises a field effect transistor having its drain and source connected between the power source and the one electrode, and receiving the control signal at its gate.

23. The apparatus of claim 21 wherein the control means includes a field effect transistor connected in a common source configuration with its drain connected to the source of power through a resistor and its source connected to the power source common return through a zener diode having a selected breakover voltage, and wherein the gate of the field effect transistor is connected to the reference node and the voltage at the drain is operably connected to the controllable conduction means to provide a voltage control signal thereto.

24. The apparatus of claim 23 wherein the control means further includes a bipolar transistor having its collector connected to the source of electrical power, its gate connected to the drain of the field effect transistor and its emitter connected to provide the control signal to the controllable conduction means.

25. The apparatus of claim 20 wherein the resistance means comprises a pair of resistors of equal resistance joined at the reference node.

26. The apparatus of claim 20 wherein the switchable means includes means for controlling the current passed therethrough to a selected level when in its conducting state.

27. The apparatus of claim 26 wherein the switchable means further comprises means responsive to an input voltage pulse for switching from the non-conducting to the conducting state and for controlling the level of the current passed therethrough in the conducting state to be directly proportional to the magnitude of the voltage of the input pulse.

28. The apparatus of claim 20 wherein the switchable means includes a bipolar transistor having its collector connected to one of the electrodes and its emitter connected to a load resistor connected to the common return and including means responsive to a voltage input pulse signal which may be provided thereto and to the voltage at the emitter for providing input current to the base of the transistor to control the current passing between the collector and emitter at a selected current level proportional to the voltage of the pulse input.

29. The apparatus of claim 28 wherein the means responsive to an input pulse signal for providing input current to the base of the bipolar transistor includes an operational amplifier having its output connected to the base of the transistor and receiving the input pulse signal at a first non-inverting input terminal and further connected to the emitter of the transistor through a voltage divider to provide a feedback voltage signal to a second inverting input of the operation amplifier.

* * * * *